United States Patent
Monteiro

(10) Patent No.: US 10,655,092 B2
(45) Date of Patent: May 19, 2020

(54) EXFOLIATING MINERAL SOAP

(71) Applicant: Maureen E Monteiro, Chevy Chase, MD (US)

(72) Inventor: Maureen E Monteiro, Chevy Chase, MD (US)

(*) Notice: Subject to any disclaimer, the term of this patent is extended or adjusted under 35 U.S.C. 154(b) by 0 days.

(21) Appl. No.: 15/866,806

(22) Filed: Jan. 10, 2018

(65) Prior Publication Data

US 2018/0127690 A1   May 10, 2018

Related U.S. Application Data

(63) Continuation-in-part of application No. 14/599,862, filed on Jan. 19, 2015, now abandoned.

(60) Provisional application No. 61/929,301, filed on Jan. 20, 2014.

(51) Int. Cl.

| | |
|---|---|
| C11D 1/00 | (2006.01) |
| C11D 9/20 | (2006.01) |
| C11D 9/10 | (2006.01) |
| A61K 8/34 | (2006.01) |
| A61K 8/92 | (2006.01) |
| A61K 8/02 | (2006.01) |
| A61Q 19/10 | (2006.01) |
| A61K 8/19 | (2006.01) |
| A61K 8/20 | (2006.01) |

(52) U.S. Cl.
CPC .............. *C11D 9/20* (2013.01); *A61K 8/0216* (2013.01); *A61K 8/19* (2013.01); *A61K 8/20* (2013.01); *A61K 8/34* (2013.01); *A61K 8/922* (2013.01); *A61Q 19/10* (2013.01); *C11D 9/10* (2013.01); *A61K 2800/28* (2013.01)

(58) Field of Classification Search
None
See application file for complete search history.

(56) References Cited

U.S. PATENT DOCUMENTS

| | | | | |
|---|---|---|---|---|
| 5,510,050 A | * | 4/1996 | Dunbar ................ | C11D 17/006 510/153 |
| 2009/0149361 A1 | * | 6/2009 | Adkison ................ | A61K 8/02 510/119 |

* cited by examiner

*Primary Examiner* — Necholus Ogden, Jr.
(74) *Attorney, Agent, or Firm* — Capitol City TechLaw, PLLC; Samuel P. Burkholder

(57) ABSTRACT

An exfoliating mineral soap has a cleansing surfactant base, a first quantity of exfoliating agent, a second quantity of exfoliating agent and a muscle relaxing agent. The first quantity of exfoliating agent is dispersed throughout the cleansing surfactant base. The second quantity of exfoliating agent is concentrated on a first external surface of the cleansing surfactant base. The muscle relaxing agent is concentrated on a second external surface of the cleansing surfactant base. The muscle relaxing agent has a magnesium chloride.

10 Claims, 8 Drawing Sheets

EXFOLIATING MINERAL SOAP

The current application claims a priority to the U.S. Provisional Patent application Ser. No. 61/929,301 filed on Jan. 20, 2014, and a priority to the U.S. Non-Provisional patent application Ser. No. 14/599,862 filed on Jan. 19, 2015.

FIELD OF THE INVENTION

The present invention relates generally to a soap. More particularly, the present invention relates to an exfoliating mineral soap which is made from composite ingredients in order to exfoliate, cleanse and relax through the skin of a user when properly applied.

BACKGROUND OF THE INVENTION

The skin is the protective coating that envelopes the human's whole body and is responsible for the protection of the organs inside. Skin also regulates body temperature through sweat glands and works in conjunction with the nervous system to alert the body of various environmental conditions. Skin further creates and absorbs essential vitamins and minerals necessary for the body's survival from environmental and topical elements. Skin consists of three different layers: the epidermis, the dermis and the subcutaneous layer. The epidermis portion that is exposed to the environment comprises dead skin cells that are constantly being shed and replaced by newer skin cells. These new cells produced in the lower layers of the epidermis every 28 days. Proper hygiene allows the skin to function optimally. Dirt and dust settles and adheres to the skin adversely affecting the temperature regulating properties of skin. To remove such dust and dirt, washing and exfoliating the epidermal layer on a regular basis is required. Soap is typically chosen to clean the epidermal layer. Most bars of soap comprise natural oils or fats that have been treated with sodium hydroxide or other strong alkali. During the cleaning process, soap acts as an emulsifying agent and traps insoluble particles resulting in a water-soluble micelle which can be washed away simply with water. Soap has been known to be used since the ancient Babylon civilization where alkali and cassia oil was used instead. Since then, soap has evolved to embody a variety of different designs and compositions. Through the use of soap, a user washes the outer layer removing dirt, debris, and other small particles from the skin; it does not remove old dead skin cells and an excess of dead cells on the outer layer of the skin clogs pores, produces acne, and traps dirt. Exfoliating once or twice a week sheds these unwanted dead cells from the skin and produces a healthy growing environment for new born skin cells. This can be achieved through chemical or mechanical means. Chemical exfoliates utilize acidic properties of various compounds to weaken the cohesive properties of the skin cells in order to remove them. Mechanical means, on the other hand, utilize physical agitation to manually scrub dead skins off the top epidermal layer.

The majority of the population only washes their skin with soap. Most do not regularly exfoliate. The importance of exfoliation is not well known in the modern community due to lack of awareness and access to facilities. The present invention seeks to provide a product which contains exfoliation qualities, soap qualities and mineral absorption qualities. The combining of the three features encourages proper skin hygiene in a safe, convenient, and simple manner. Soaking in warm or hot water causes the pores to expand. Toxins are released from the body through the pores while minerals are received through the pores to enhance the relaxing effect. Using the exfoliating mineral body soap of the present invention to bathe and/or soak offers a refreshing feeling, cleansing toxins, and removing particulates from the body of the user. The muscle relaxing agent is allowed increased affect once the skin is exfoliated.

DETAIL DESCRIPTIONS OF THE INVENTION

All illustrations of the drawings are for the purpose of describing selected versions of the present invention and are not intended to limit the scope of the present invention.

The present invention is for providing an exfoliating mineral soap 100 which removes small particles and dead skin cells from the outer layer of the skin of a user to allow added affect of a muscle relaxing agent. Abrasive materials are dispersed throughout a cleaning base such that the present invention is able to effectively clean, exfoliate and mineralize the user's skin. The cleansing base emulsifies dust and small particulates such that the user is able to use water to wash away water insoluble compounds present on their skin.

Figure 1:
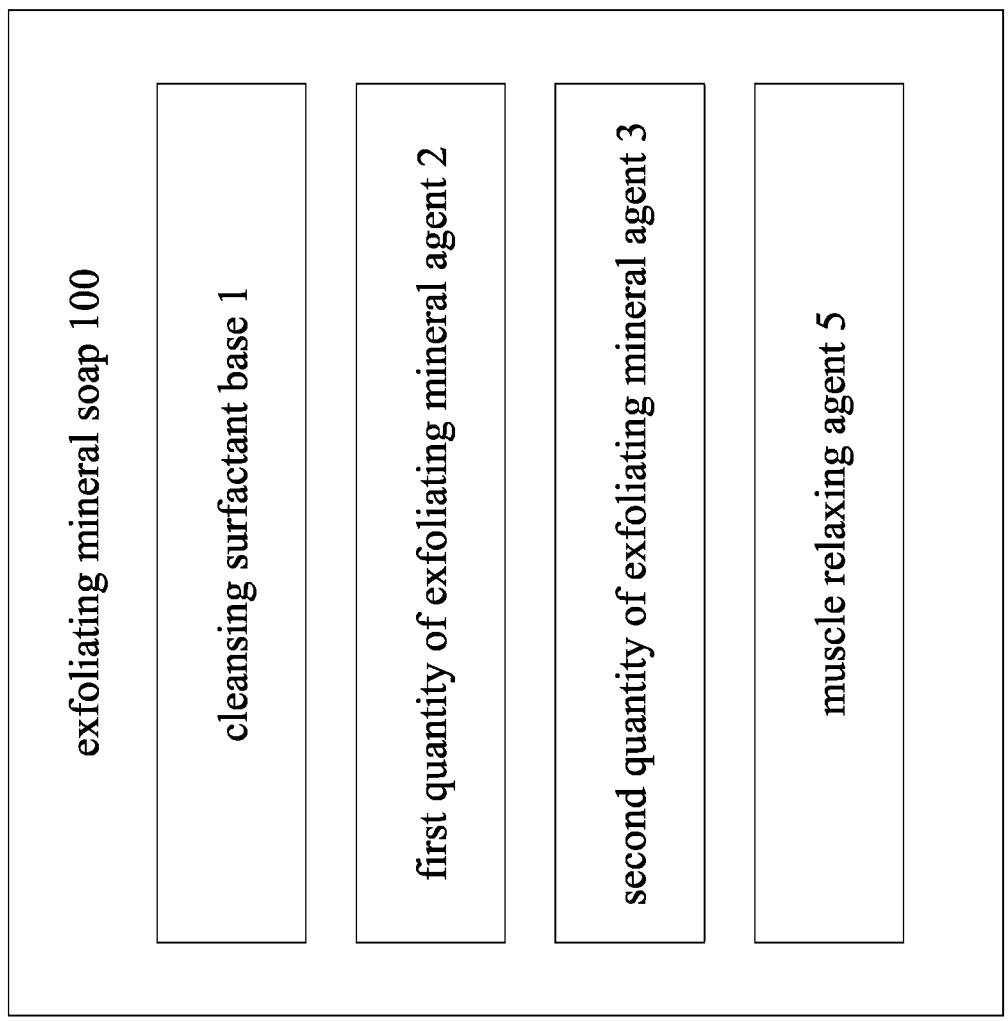
FIG. 1 is a block diagram illustrating components of an exfoliating mineral soap of the present invention.
Figure 2:
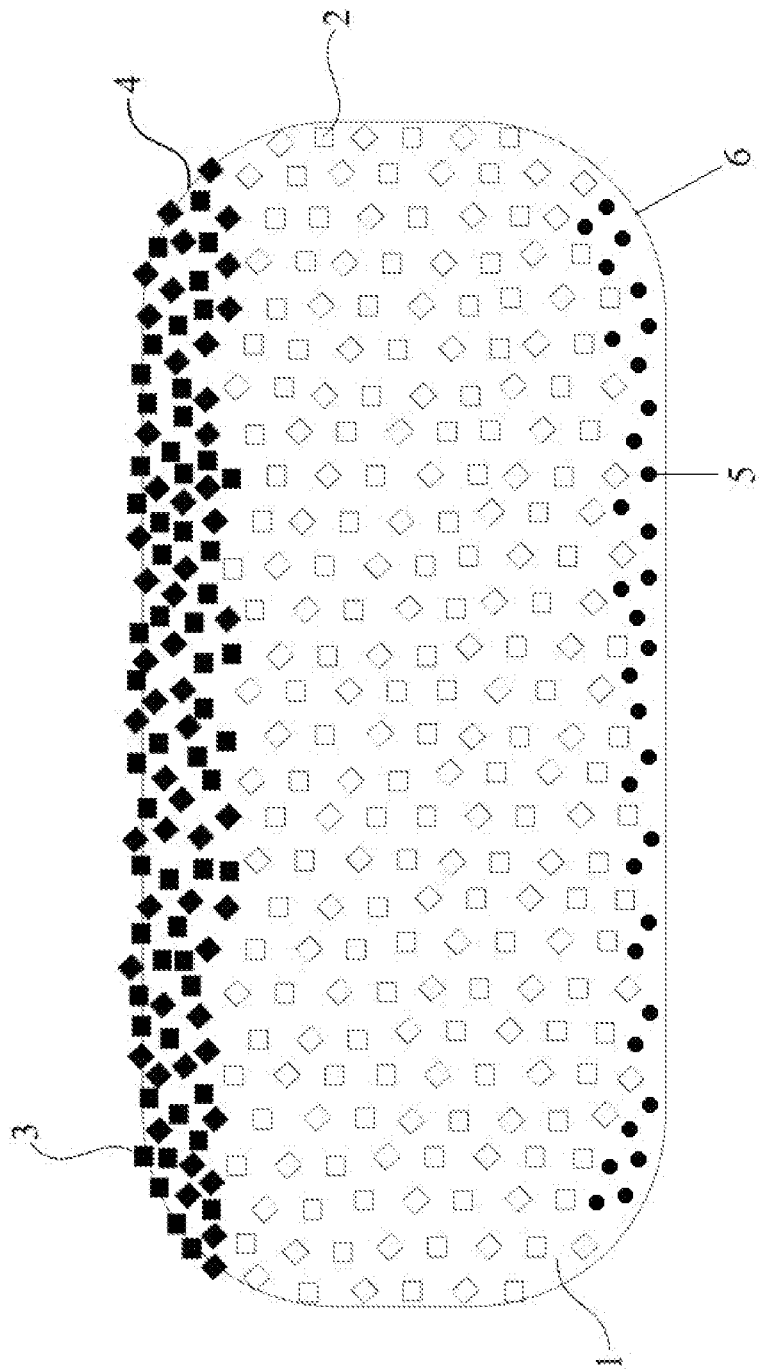
FIG. 2 is a schematic view illustrating the exfoliating mineral soap of the present invention.

In accordance with FIGS. 1-2, according to an embodiment of the present invention, an exfoliating mineral soap 100 comprises a cleansing surfactant base 1, a first quantity of exfoliating agent 2, a second quantity of exfoliating agent 3 and a muscle relaxing agent 5. The cleansing surfactant base 1 provides a compound that suspends the first quantity of exfoliating agent 2, the second quantity of exfoliating agent 3 and the muscle relaxing agent 5, as well as cleans and emulsifies dust and other particulates to be removed from the user's skin through additional use of water. The first quantity of exfoliating agent 2 and the second quantity of exfoliating agent 3 each is an abrasive material which removes dead skin from the user. The first quantity of exfoliating agent 2 is dispersed throughout the cleansing surfactant base 1 with a first concentration. As the cleansing surfactant base 1 is being dissolved through use, more of the first quantity of exfoliating agent 2 is exposed over time maintaining a relatively constant abrasiveness of slight variance. The second quantity of exfoliating agent 3 is concentrated on a first external surface 4 of the cleansing surfactant base 1 with a second concentration, which allows the user to target and exfoliate specific sections of their skin. The second concentration is larger than the first concentration, such that the first quantity of exfoliating agent 2 and the second quantity of exfoliating agent are conjointly dispersed throughout the cleansing surfactant base 1 in a nonuniform manner. The muscle relaxing agent 5 is concentrated on a second external surface 6 of the cleansing surfactant base 1. The first external surface 4 and the second external surface 6 are located opposite to each other. In the preferred embodiment, the cleansing surfactant base 1 is approximately 70% by volume of the present invention, the first quantity of exfoliating agent 2 and the second quantity of exfoliating agent 3 encompass approximately 25% by volume of the present invention, and the muscle relaxing agent 5 is approximately 5% by volume of the present invention.

Figure 3:
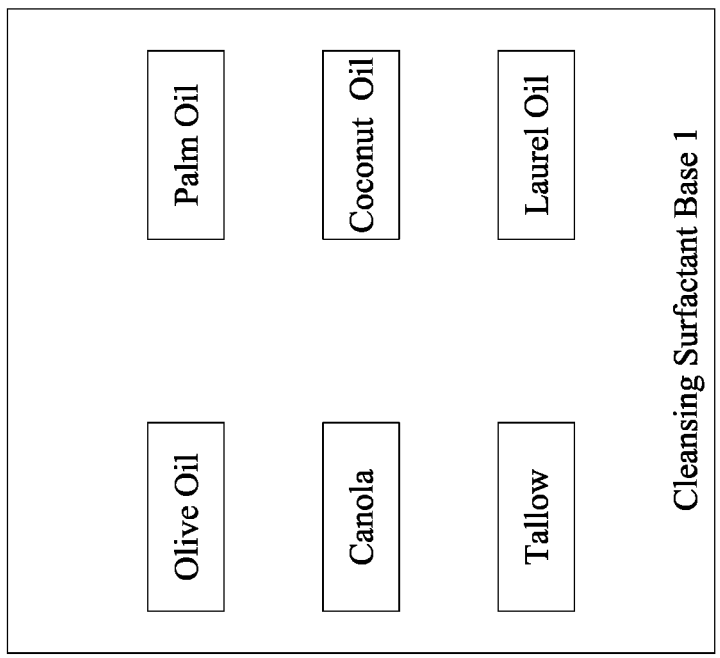
FIG. 3 is a block diagram illustrating active ingredients of a cleansing surfactant base of the exfoliating mineral soap of the present invention.
Figure 5:
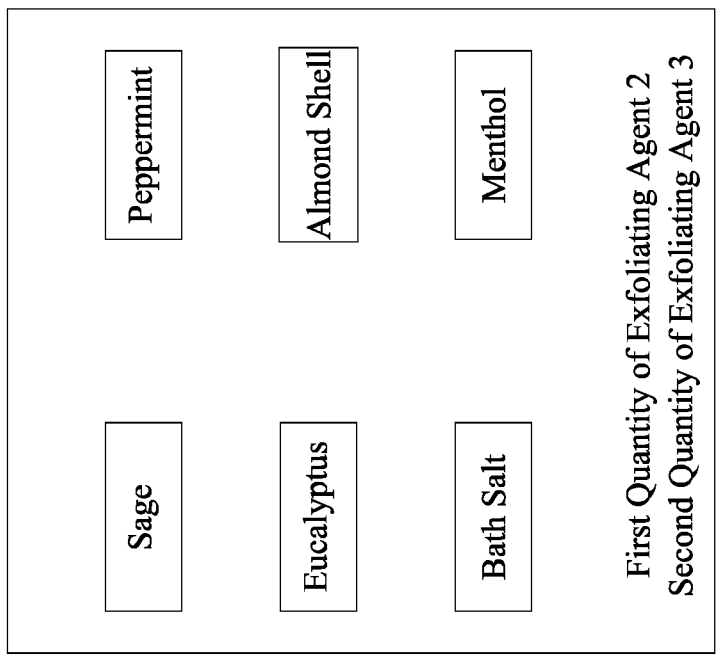
FIG. 5 is a block diagram illustrating ingredients of a first quantity of exfoliating agent and a second quantity of exfoliating agent of the exfoliating mineral soap of the present invention.

The cleansing surfactant base 1 contains active ingredients selected from a group consisting of palm, coconut, olive, canola, tallow, laurel oils, and combinations thereof, as detailed in FIG. 3. These compounds have been proven effective for cleansing the epidermal layer and formulating a solid soap base. As shown in FIG. 5, the first quantity of exfoliating agent 2 and the second quantity of exfoliating agent 3 are selected from a group consisting of sage, eucalyptus, peppermint, bath salt, almond shell, menthol, and combinations thereof. The compounds for the first quantity of exfoliating agent 2 and the second quantity of exfoliating agent 3 create an abrasive texture. The abrasive texture is formulated by grinding these compounds into particulates and chosen from fine, medium, or course grades, average particle sizes between 68 to 140, 190 to 265 and 336 to 425 micrometers, respectively. The abrasive texture to be incorporated within the present invention for different grits is dependent on various skin types and user preference. Further, these particular ingredients provide the skin with vitamins, minerals, and similar nutritional resources as well as various health benefits. Sage is a natural disinfectant and deodorizer with healing capabilities. *Eucalyptus* oils treat acne, wounds, inflammations, burns, infections, and joint pains. Peppermint contains ingredients that activate cold-sensitive receptors in the skin and create a cooling sensation. Almond shells, extracts, and oils provide the skin with riboflavin, niacin, thiamin, pantothenic acid, vitamin B-6, folates, and a plurality of minerals. Bath salts are water soluble crystalline-type particles containing natural ingredients and nutrients that create the abrasive texture of the exfoliating mineral portion of the present invention. Some bath salts are energizing and others are soothing. Menthol is an organic compound with local anesthetic, counterirritant, and soothing qualities, ideal for a recently exfoliated epidermal layer.

Figure 4:
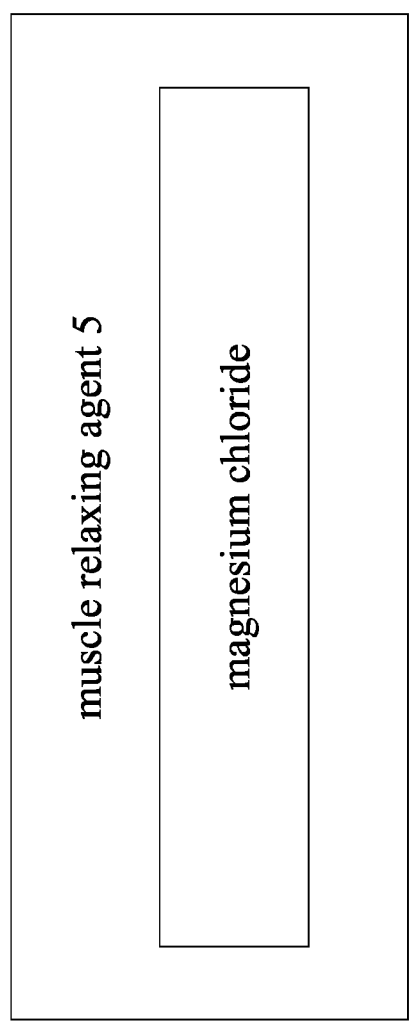
FIG. 4 is a block diagram illustrating an ingredient of a muscle relaxing agent of the present invention.

In the embodiment, the present invention comprises the muscle relaxing agent 5, as shown in FIGS. 1-2 and 4. The muscle relaxing agent 5 is water soluble and can be topically applied to the user's skin for a relaxing effect on their muscles, or the user can allow a dissolve in water for soaking purposes. Reducing pain levels and relaxing the person are performed by using the exfoliating mineral soap 100. As shown in FIG. 4, the muscle relaxing agent 5 comprises a magnesium chloride since the magnesium chloride is able to be topically absorbed through the skin, but any other topically applied muscle relaxing agent may be used.

Figure 6:
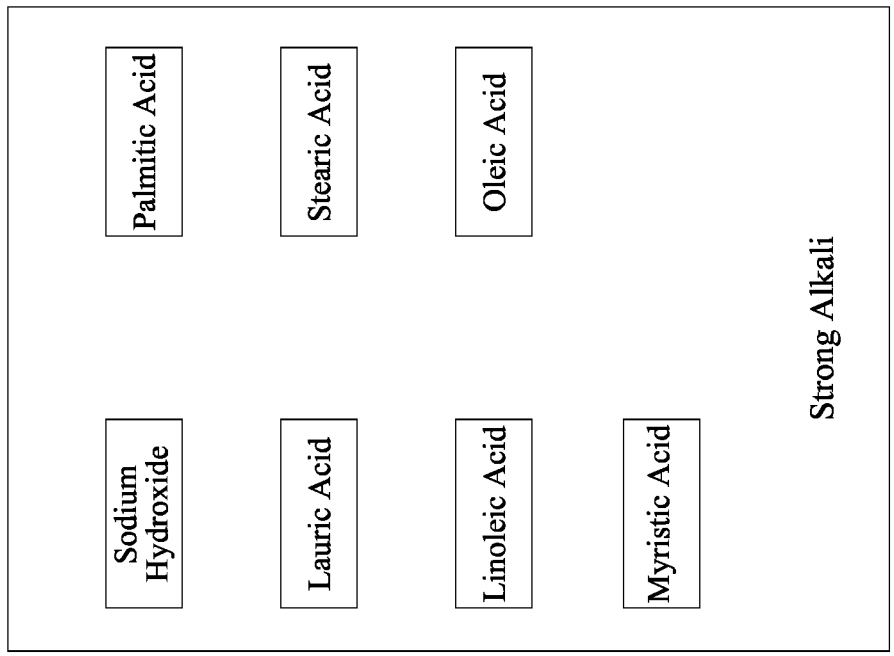
FIG. 6 is a block diagram illustrating ingredients of strong alkali of the present invention.
Figure 7:
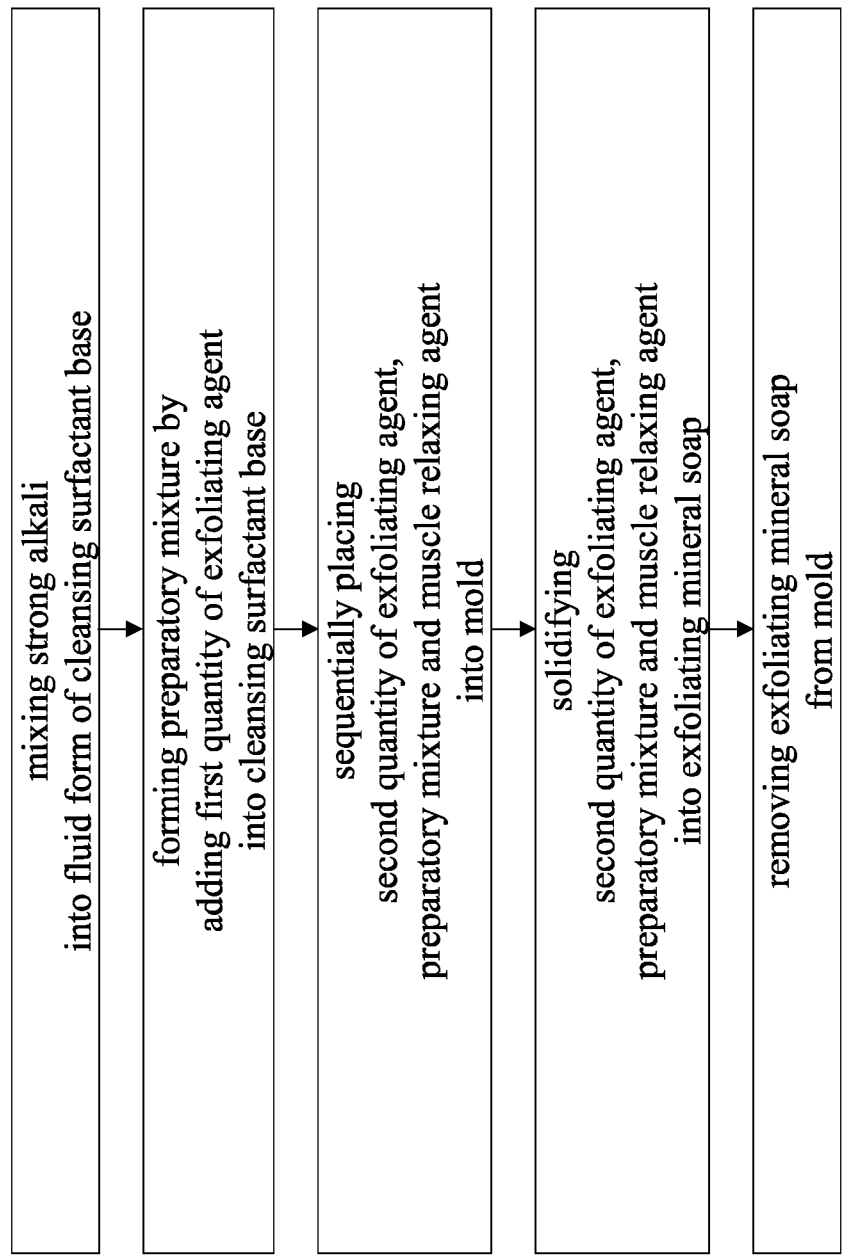
FIG. 7 is a flow diagram illustrating a method of manufacturing the exfoliating mineral soap of the present invention.

In order to manufacture the present invention detailed in FIG. 7, a user first mixes a strong alkali into a fluid form of the cleansing surfactant base 1. The strong alkali reacts with the oils and fatty active ingredients within the cleansing surfactant base 1, beginning the solidification of the present invention over a period of time. In accordance to FIG. 6, the strong alkali is selected from a group consisting of sodium hydroxide, lauric acid, myristic acid, palmitic acid, stearic acid, oleic acid, linoleic acid, and combinations thereof. These compounds have been found effecting in forming a water-soluble micelle which binds and removes particulates from the user's skin. As the exfoliating mineral soap 100 begins the solidifying reaction, the first quantity of exfoliating agent 2 is added and homogeneously mixed with the cleansing surfactant base 1 forming a preparatory mixture.

Figure 8:
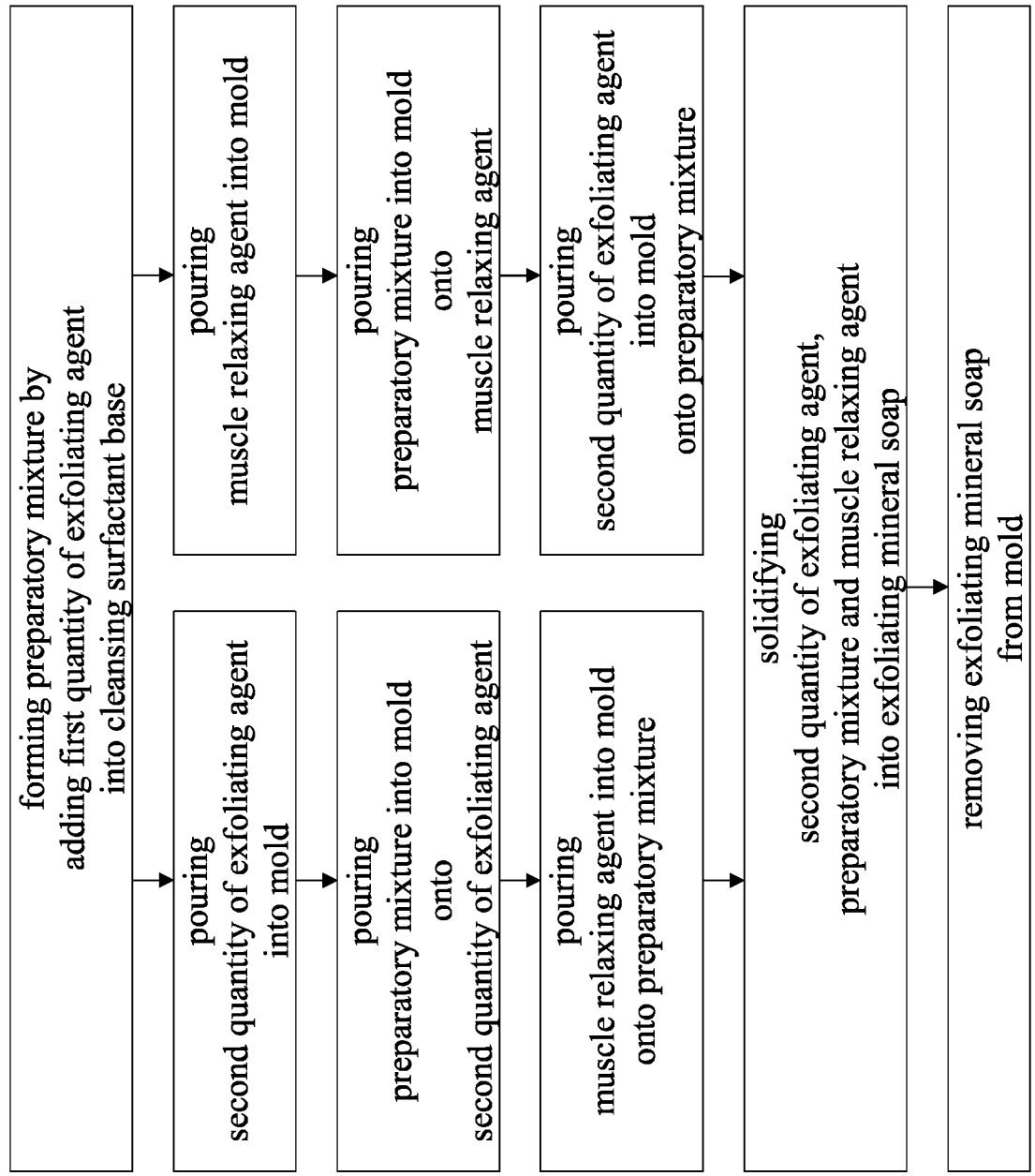
FIG. 8 is a flow diagram illustrating two different processes for adding the second quantity of exfoliating agent to a preparatory mixture of the present invention.

As shown in FIG. 8, the method of manufacture has two different processes for placing the second quantity of exfoliating agent 3, the preparatory mixture and the muscle relaxing agent 5 into a mold, while the preparatory mixture is still in a liquid form, in accordance to FIG. 7. The mold is an impression of the final form of the exfoliating mineral soap 100. In one process, the second quantity of exfoliating agent 3 is poured into the mold, the preparatory mixture is poured into the mold onto the second quantity of exfoliating agent 3, and the muscle relaxing agent 5 is poured into the mold onto the preparatory mixture. In this process, the second quantity of exfoliating agent 3 is dispersed on the first external surface 4 of the solid cleansing surfactant base 1 and the muscle relaxing agent 5 is dispersed on the second external surface 4 of the solid cleansing surfactant base 1 in the form of the mold. In the other process, the muscle relaxing agent 5 is poured into the mold, the preparatory mixture is poured into the mold onto the muscle relaxing agent 5, and the second quantity of exfoliating agent 3 is poured into the mold onto the preparatory mixture. In this alternate process, the second quantity of exfoliating agent 3 is dispersed on the first external surface 4 of the solid cleansing surfactant base 1 and the muscle relaxing agent 5 is dispersed on the second external surface 4 of the solid cleansing surfactant base 1 in the form of the mold. Once the second quantity of exfoliating agent 3, the preparatory mixture and the muscle relaxing agent 5 are present within the mold, they are solidified through a drying process into the exfoliating mineral soap 100. Finally, when the exfoliating mineral soap 100 is solidified, the exfoliating mineral soap 100 is removed from the mold and ready for packaging or direct use.

The following description presents the research on the physiological and psychological effects of bathing with the exfoliating mineral soap 100 created by the inventor.

Research in stress reduction indicates there are four broad categories of stressors: cataclysmic events, stressful life events, daily hassles and ambient stressors. Unresolved stress can have detrimental health consequences. Interest in stress reduction and relaxation has led people to practice stress reduction strategies and techniques i.e. yoga and meditation. It is asserted that by practicing yoga and meditation, practitioners can cultivate mindfulness, awareness of the body, awareness of feelings, awareness of mental thoughts, and awareness of truths to help explain life experience. Life is complex, and many find that the simple, daily ritual of bathing helps reduce stress.

Water used in the human ritual of bathing is the ideal environment for cleansing the body of harmful elements. The value of water in preventing disease was recognized by ancient peoples, and baths were used by them to a far greater extent than in modern times. Bathing not only cleanses the skin, but also is known to aide in the release of toxic matter when exfoliation is added. The cleansing process is compounded when the body is submerged in warm or hot water aiding musculoskeletal conditions, i.e., tension, fatigue, strain, pain.

According to the American Academy of Dermatology, exfoliation is the process of removing the top layer of dead skin cells and can be achieved chemically, by applying an acid that dissolves those cells, or mechanically, by using a brush or scrub to physically remove the cells. It is stated that exfoliation can improve your skin's appearance and make topical treatments more effective, but every type of exfoliation may not work for every skin type.

Exfoliation sometimes referred to as desquamation is one of the processes by which skin maintains its health and vitality, as nutrients and moisture are continuously replaced on the surface of the skin when dead skin cells are removed naturally. If the stratum corneum gets too dry, the skin can become itchy, scaly, inflamed, leathery and unattractive.

In the present invention, the impact of the muscle relaxing agent 5 which preferably comprises the magnesium chloride when applied to the surface of skin increases the healing process. Magnesium chloride in a hot bath will impart a very relaxing soak while delivering a vast amount of magnesium to the cells, great for restless leg syndrome.

This research study examined the experience of ten participants of varying ages who applied the exfoliating mineral soap 100 of the present invention during bathing. The exfoliating mineral soap 100 created the inventor contains the magnesium chloride. Magnesium chloride is a highly soluble, potent form of magnesium for fast-acting topical uses. It is suggested that magnesium chloride is a most important and vital mineral required for life. Without magnesium chloride, the human body would be unable to maintain fluids in blood vessels, conduct nerve transmissions, move muscles, or maintain proper kidney function.

Recruited participants using a network selection strategy. A network selection strategy is defined as the ability of the researcher to use personal contacts to locate other potential participants for the study. Through contact with members of varying ages at a local recreation center, participants were identified and recruited to participate in this research study. Participants were fully informed of the research procedures and risks, and their informed consent was obtained.

Table 1 provides demographic information of the research participants.

TABLE 1

| Participant # | P1 | P2 | P3 | P4 | P5 | P6 | P7 | P8 | P9 | P10 |
|---|---|---|---|---|---|---|---|---|---|---|
| Gender | F | F | F | F | F | F | F | F | M | M |
| Age | 37 | 49 | 35 | 39 | 32 | 42 | 65 | 63 | 27 | 53 |

For the research study, the following steps were followed. First, participants were recruited, and participants consent was obtained. Second, participants were informed about the exfoliating mineral soap 100 and how to use it. Third, required participants to keep a journal to record any effects after using the exfoliating mineral soap 100 in preparation to share responses during informal meetings. Fourth, after the introduction and instructions on how to use the exfoliating mineral soap 100, each participant received three bars of the exfoliating mineral soap 100.

Participants responded in writing and in conversation. The responses were the data gathered to examine their direct experience to bathing with the exfoliating mineral soap 100. Additionally, the data gathered, helped to answer the research question, "To what extent has the experience of bathing with the exfoliating mineral soap 100 affected you?"

Table 2 illustrates participant responses to and effects of using the exfoliating mineral soap 100 while bathing.

TABLE 2

| Participant | Response | Effect |
|---|---|---|
| P1 - Female, 37 yr. old | "While immersed in the water my legs slightly tingled. It was as if the blood was moving faster than normal." | Increased stimulation |
| P2 - Female, 49 yr. old | "My skin feels so soft." | Soft skin |
| P3 - Female, 35 yr. old | "I slept better than I have in years, and had more energy the next day." | Better Sleep Increase in energy Well rested |
| P4 - Female, 39 yr. old | "Oh, how relaxing." | Relaxation |
| P5 - Female, 32 yr. old | "This is nature's medicine. I want more." | Therapeutic |
| P6 - Female, 42 yr. old | "I think I need to bath more. The ache in my shoulder is gone." | Increased awareness of the value of bathing |
| P7 - Female, 37 yr. old | "Can I have more EBS.? It makes me feel so good." | Desire for more exfoliating mineral soaps Feel good |
| P8 - Female, 67 yr. old | "The EBS fell apart, but it my skin felt like a baby's bottom." | Soft skin |
| P9 - Male, 53 yr. old | "Hey, I like it. You might be onto something here." | Positive response, Supportive |
| P10 - Male, 27 yr. old | "What a good experience, it felt so relaxing. I want to share it with my mom and a friend." | Good feeling, relaxed, and inspired to share |

Participants indicate that bathing with the exfoliating mineral soap 100 had beneficial effects. Data suggests that bathing aids physical relaxation. The relaxation participants perceived by bathing with the exfoliating mineral soap 100 can be described using emic responses shown in Table 2.

Research data suggests the physiological effects of bathing while using the exfoliating mineral soap 100 could rejuvenate and enhance the health of the skin. Research has also shown significant increases in sleepiness at bed-time.

Further, the participant responses can be categorized thematically as follows: skin softness, (exfoliation) muscle tension reduction (magnesium chloride), and improved states of mind (calming, soothing, relaxing). This study of with the exfoliating mineral soap 100 provides valuable insights into the relationship between bathing and human health.

Research needs to be conducted longitudinally with participants while bathing. Additionally, research on the use of the exfoliating mineral soap 100 with participants accustomed to showering should be conducted. Research conducted on the experience of participants who use the exfoliating mineral soap 100 showering, and as part of other daily personal hygiene routines would provide additional data and increase understanding of the impact the exfoliating mineral soap 100 has on overall well-being.

Although the invention has been explained in relation to its preferred embodiment, it is to be understood that many other possible modifications and variations can be made without departing from the spirit and scope of the invention as hereinafter claimed.

What is claimed is:

1. A solid exfoliating mineral soap comprising:
   a solidified cleansing surfactant base;
   a first quantity of exfoliating agent;
   a second quantity of exfoliating agent; and
   a water soluble muscle relaxing agent;

the first quantity of exfoliating agent being uniformly dispersed throughout the cleansing surfactant base with a first concentration;

the second quantity of exfoliating agent being concentrated on a first external surface of the cleansing surfactant base with a second concentration;

the second concentration being larger than the first concentration so as to render the first quantity of exfoliating agent and the second quantity of exfoliating agent being conjointly dispersed throughout the cleansing surfactant base in a nonuniform manner;

the water soluble muscle relaxing agent being concentrated on a second external surface of the cleansing surfactant base, the first external surface and the second external surface being located opposite to each other; and the water soluble muscle relaxing agent comprising magnesium chloride.

2. The solid exfoliating mineral soap as claimed in claim 1 comprising:

the first quantity of exfoliating agent and the second quantity of exfoliating agent each being an abrasive material.

3. The solid exfoliating mineral soap as claimed in claim 2 comprising:

the abrasive material being fine grade particulate with a particle size ranging from 68 to 140 micrometers.

4. The solid exfoliating mineral soap as claimed in claim 2 comprising:

the abrasive material being medium grade particulate with a particle size ranging from 190 to 265 micrometers.

5. The solid exfoliating mineral soap as claimed in claim 2 comprising:

the abrasive material being coarse grade particulate with a particle size ranging from 336 to 425 micrometers.

6. The solid exfoliating mineral soap as claimed in claim 1 comprising:

the water soluble muscle relaxing agent being about 5% by volume of the exfoliating mineral soap.

7. The solid exfoliating mineral soap as claimed in claim 1 comprising:

the first quantity of exfoliating agent and the second quantity of exfoliating agent being about 25% by volume of the exfoliating mineral soap.

8. The solid exfoliating mineral soap as claimed in claim 1 comprising:

the cleansing surfactant base being about 70% by volume of the exfoliating mineral soap.

9. The solid exfoliating mineral soap as claimed in claim 1 comprising:

the cleansing surfactant base comprising ingredients selected from a group consisting of palm oil, coconut oil, olive oil, canola, tallow, laurel oil, and combinations thereof.

10. The solid exfoliating mineral soap as claimed in claim 1 comprising:

the first quantity of exfoliating agent and the second quantity of exfoliating agent each comprising ingredients selected from a group consisting of sage, eucalyptus, peppermint, almond shell, menthol, and combinations thereof.

* * * * *